(12) United States Patent
Hummer et al.

(10) Patent No.: US 11,207,513 B2
(45) Date of Patent: Dec. 28, 2021

(54) CONNECTION PIECE FOR PRODUCING A LIQUID CONNECTION BETWEEN LIQUID-CONVEYING LINES, AND MEDICAL APPLIANCE WITH SUCH A CONNECTION PIECE

(71) Applicant: FRESENIUS MEDICAL CARE DEUTSCHLAND GMBH, Bad Homburg (DE)

(72) Inventors: Dirk Hummer, Hirschfeld (DE); Olaf Nicholas, Kitzingen (DE); Paul Aschenbrenner, Schonungen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 208 days.

(21) Appl. No.: 16/348,159

(22) PCT Filed: Oct. 30, 2017

(86) PCT No.: PCT/EP2017/077829
§ 371 (c)(1),
(2) Date: May 8, 2019

(87) PCT Pub. No.: WO2018/086950
PCT Pub. Date: May 17, 2018

(65) Prior Publication Data
US 2019/0262601 A1 Aug. 29, 2019

(30) Foreign Application Priority Data
Nov. 10, 2016 (DE) .................... 10 2016 013 334.1

(51) Int. Cl.
*A61M 39/10* (2006.01)
*A61M 1/14* (2006.01)
(Continued)

(52) U.S. Cl.
CPC .............. *A61M 39/10* (2013.01); *A61M 1/14* (2013.01); *A61M 1/1621* (2014.02);
(Continued)

(58) Field of Classification Search
CPC .. A61M 39/10; A61M 1/1656; A61M 1/1621; A61M 1/14; A61M 2039/0267;
(Continued)

(56) References Cited

U.S. PATENT DOCUMENTS

2013/0245530 A1    9/2013   Brandi et al.

FOREIGN PATENT DOCUMENTS

DE           3543233 A1    6/1987
DE    102013107323 A1 *   1/2015   .............. A61M 1/14
(Continued)

OTHER PUBLICATIONS

International Search Report and Written Opinion issued in corresponding International Patent Application No. PCT/EP2017/077829 (with English translation of International Search Report) dated Jan. 30, 2018 (12 pages).
(Continued)

*Primary Examiner* — Waqaas Ali
(74) *Attorney, Agent, or Firm* — Kilyk & Bowersox, P.L.L.C.

(57) ABSTRACT

The invention relates to a connecting piece for establishing a fluid connection between fluid-conducting lines for installation in a cut-out in a housing part of a medical device, in particular a dialysis unit. Furthermore, the invention relates to a medical device, in particular a dialysis unit, comprising a housing that comprises a housing part having a cut-out into which a connecting piece of this type is inserted. The connecting piece 13 according to the invention comprises a tubular body 18 that is made of an electrically conductive material and can be inserted into the cut-out 23 in the
(Continued)

Figure 1:
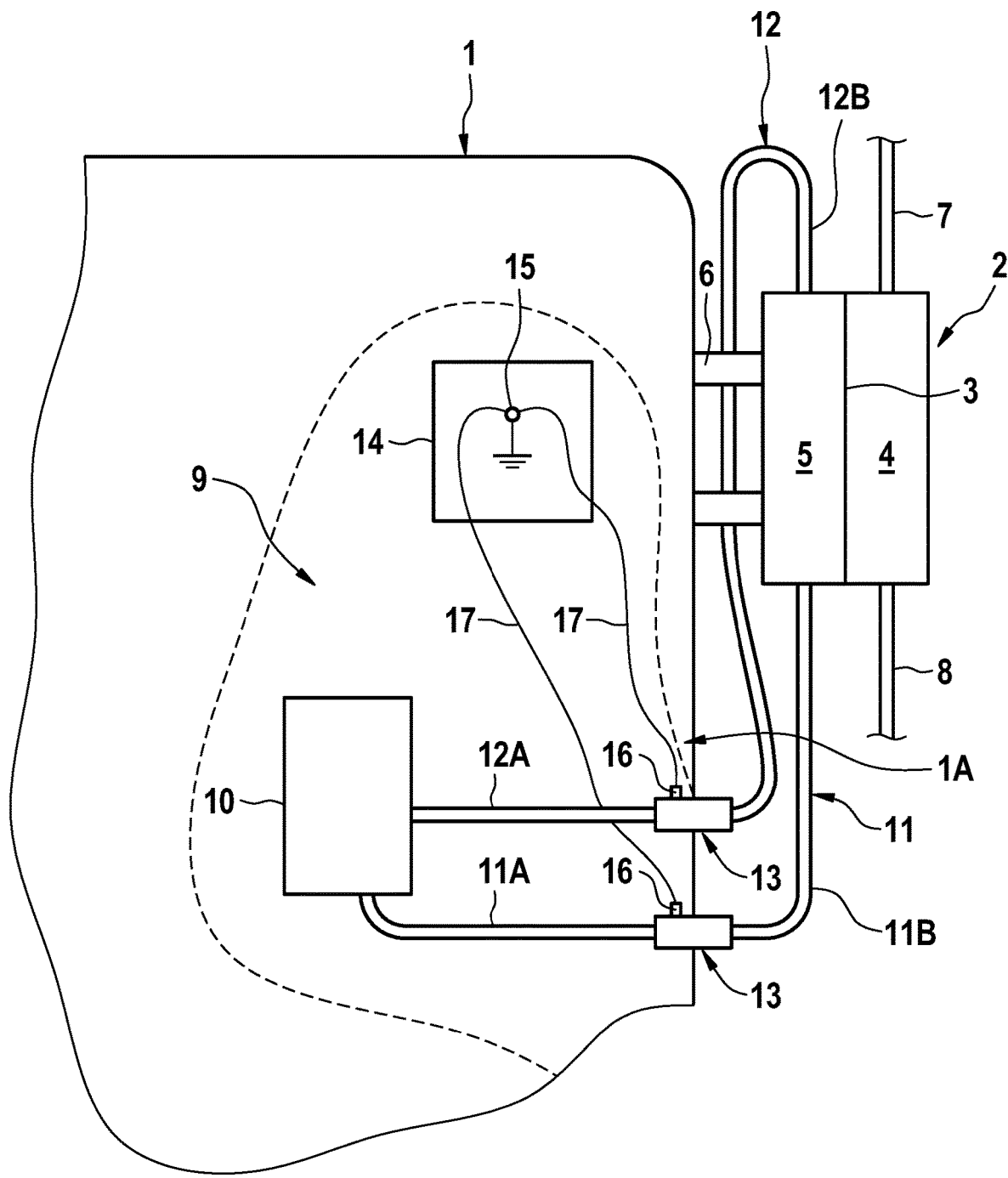

housing part 1A, the end pieces 19, 20 of which body are designed for the attachment of the fluid-conducting lines. The connecting piece 13 is distinguished by a terminal part 16 for attaching an electrical protective conductor or equipotential bonding system, the terminal part 16 being electrically conductively connectable or connected to the tubular body 18. The terminal part 16 allows an electrical connection cable 17 to be directly attached to a protective conductor 15 (PE conductor).

15 Claims, 3 Drawing Sheets

(51) Int. Cl.
    *A61M 1/16*    (2006.01)
    *A61M 39/02*    (2006.01)

(52) U.S. Cl.
    CPC ... *A61M 1/1656* (2013.01); *A61M 2039/0267* (2013.01); *A61M 2039/1022* (2013.01); *A61M 2205/0233* (2013.01)

(58) Field of Classification Search
    CPC ... A61M 2039/1022; A61M 2205/0233; F16L 11/1185; F16L 11/127; F16L 11/112; F16L 11/16; F16L 25/01; F16L 2011/047; F16L 11/118; F16L 9/125; F16L 11/12
    See application file for complete search history.

(56) References Cited

FOREIGN PATENT DOCUMENTS

| | | |
|---|---|---|
| DE | 102013107323 A1 | 1/2015 |
| DE | 102014200440 A1 | 7/2015 |
| EP | 1633428 B1 | 11/2011 |
| WO | 2004108206 A1 | 12/2004 |
| WO | 2009044220 A1 | 4/2009 |
| WO | 2013135386 A1 | 9/2013 |

OTHER PUBLICATIONS

International Preliminary Report on Patentability issued in corresponding International Patent Application No. PCT/EP2017/077829 dated May 14, 2019 (6 pages).

* cited by examiner

CONNECTION PIECE FOR PRODUCING A LIQUID CONNECTION BETWEEN LIQUID-CONVEYING LINES, AND MEDICAL APPLIANCE WITH SUCH A CONNECTION PIECE

This application is a National Stage Application of PCT/EP2017/077829, filed Oct. 30, 2017, which claims priority to German Patent Application No. 10 2016 013 334.1, filed Nov. 10, 2016.

The invention relates to a connecting piece for establishing a fluid connection between fluid-conducting lines for installation in a cut-out in a housing part of a medical device, in particular a dialysis unit. Furthermore, the invention relates to a medical device, in particular a dialysis unit, comprising a housing that comprises a housing part having a cut-out into which a connecting piece of this type is inserted.

Medical devices are known which have a fluid part that comprises fluid-conducting lines. The fluid-conducting lines are connected or attached by connecting pieces to which the lines can be attached. For the power supply, the medical devices have a power unit comprising a central protective-conductor connection that is connected to the protective-conductor system of the fixed electrical installation, which system is at earth potential. The testing of electrical devices includes the testing of the electrical resistance of the protective-conductor connection.

The known dialysis units have an extracorporeal blood circuit and a dialysate part. The extracorporeal blood circuit comprises the blood chamber of a dialyser, and the dialysate part comprises the dialysate chamber of a dialyser, which is divided into the two chambers by a semi-permeable membrane. The dialyser is generally an exchangeable unit, which is attached to the outside of the housing of the dialysis unit so as to be easily accessible.

The dialysis units may have an apparatus for producing dialysate from fresh water and concentrates that is within the housing. The fresh dialysate is fed to the dialysate chamber from the apparatus for producing dialysate via a dialysate feed line, and used dialysate is removed from the dialysate chamber via a dialysate removal line. Since the dialyser is not in the housing of the dialysis unit, the dialysate lines have to penetrate a housing part of the dialysis unit. Connecting or terminal pieces, which are also referred to as bushes, are used to attach the appropriate hose line portions.

The known connecting pieces are inserted into compatible cut-outs in a housing part of the dialysis unit. The housing part comprising the cut-out generally consists of an electrically conductive material (metal housing). The connecting pieces have a tubular body that can be inserted into the cut-out in the housing part, the end pieces of which body are designed for the attachment of the fluid-conducting lines. In general, the tubular body of the connecting pieces consists of an electrically conductive material, such that an electrical connection can be established between the dialysate and the metal housing of the dialysis unit. However, connecting pieces that are made of an electrically non-conductive material but have metal inserts are also known.

The problem addressed by the invention is to provide a connecting piece for establishing a fluid connection between fluid-conducting lines that can be easily and securely installed in a cut-out in a housing part of a medical device, in particular a dialysis unit. In particular, the problem addressed by the invention is to provide a connecting piece that allows both a rigid mechanical connection to the housing and an electrical connection to a protective conductor or an equipotential bonding system that is separate from the mechanical connection.

Another problem addressed by the invention is to provide a medical device, in particular a dialysis unit, that allows the resistance of the protective-conductor connection to be safely tested.

These problems are solved according to the invention by the features of the independent claims. The dependent claims relate to advantageous embodiments of the invention.

The connecting piece according to the invention for establishing a fluid connection between fluid-conducting lines, which piece is intended to be installed in a cut-out in a housing part of a medical device, in particular a dialysis unit, comprises a tubular body made of electrically conductive material that can be inserted into the cut-out in the housing part, the end pieces of which body are designed for the attachment of the fluid-conducting lines. The end pieces may be designed as terminal pieces to which hose lines can be attached. For example, the hose lines can be easily slid onto the end pieces. It is however possible for the end pieces to have plugs or sockets, or other connectors.

The connecting piece according to the invention is distinguished by a terminal part for attaching an electrical protective conductor or equipotential bonding system, the terminal part being electrically conductively connectable or connected to the tubular body. The terminal part allows an electrical connection line to be directly attached to a protective conductor (PE conductor) or an equipotential bonding system. It is advantageous that the protective-conductor connection is separate from the mechanical connection of the connecting piece to the housing part. Even if the mechanical connection is broken, the earthing required for the electrical safety of the medical device still remains.

A preferred embodiment of the connecting piece according to the invention provides that the terminal part is a ring cable lug that can be screwed to the tubular body. The tubular body preferably comprises a circumferential shoulder to which an external thread is attached. When the ring cable lug is screwed to a nut that is screwed to the external thread, the ring cable lug can be securely clamped between the circumferential shoulder and the nut.

The terminal part may, however, also be a terminal lug that is electrically conductively connected to the tubular body. The terminal lug may for example be soldered to the tubular body. In this embodiment, a screwed connection is thus omitted.

In a particularly preferred embodiment, the tubular body comprises, between the end pieces, a flange by means of which the tubular body can be supported on the housing part, and comprises a securing part that can be attached to the tubular body such that the tubular body is secured in the cut-out in the housing part in the axial direction. As a result, the connecting piece is securely mechanically connected to the housing part.

In an embodiment in which the housing of the medical device consists of an electrically conductive material, which is generally the case, the flange of the tubular body has an inner flange part that is formed in one piece with the tubular body and an outer flange part that comprises a cut-out into which the inner flange part can be inserted. The tubular body can then be supported on the housing part by the outer flange part. Since the outer flange part consists of an electrically non-conductive material, the tubular body is insulated from the housing part made of electrically conductive material. As a result, there is no electrical connection between the terminal part and the housing. This is advantageous in that, during a test of the protective-conductor connection, the resistance between the terminal part and the protective-conductor connection can be directly measured without another electrical connection, for example via other housing parts, possibly distorting the measurement result.

If the housing part of the medical device consists, however, of an electrically non-conductive material, for example is a plastics housing, it is not necessary to design the flange in two pieces so as to have an insulating part.

In another particularly preferred embodiment, the inner flange part is secured against twisting in the outer flange part. This ensures that an electrical connection cable attached to the terminal part cannot become detached by the connecting piece twisting in the housing part.

It can be secured against twisting by the two components having a non-round cross section. The outer flange part preferably comprises a polygonal cut-out, and the inner flange part comprises a polygonal peripheral surface.

The securing part is preferably a securing ring, which can be easily fitted onto the tubular body. The securing ring preferably consists of metal. By inserting a washer made of an electrically non-conductive material between the metal securing ring, which is electrically connected to the tubular body, and the flange part of the tubular body, the tubular body can be insulated from the housing part. The securing ring may also be made of plastics material, however. An additional plastics washer for electrical insulation can then be omitted. However, the use of a plastics securing ring requires said ring to meet the mechanical demands such that the connecting piece is mechanically connected to the housing so as to be secured against twisting and electrically insulated.

The medical device according to the invention has a power unit comprising a central protective-conductor connection, which is electrically connected to the terminal part of the connecting piece by an electrical connection cable. The connecting piece according to the invention is intended for a medical device that comprises a fluid part having fluid-conducting lines, the fluid-conducting lines being attached to the end pieces of the connecting piece. The medical device is in particular a dialysis unit that comprises a dialysate part having a dialysate feed line that leads to a dialyser and a dialysate removal line that leads away from the dialyser, one portion of the dialysate feed line or dialysate removal line being attached to one end piece and another portion of the dialysate feed line or dialysate removal line being attached to the other end piece of the connecting piece.

Figure 2:
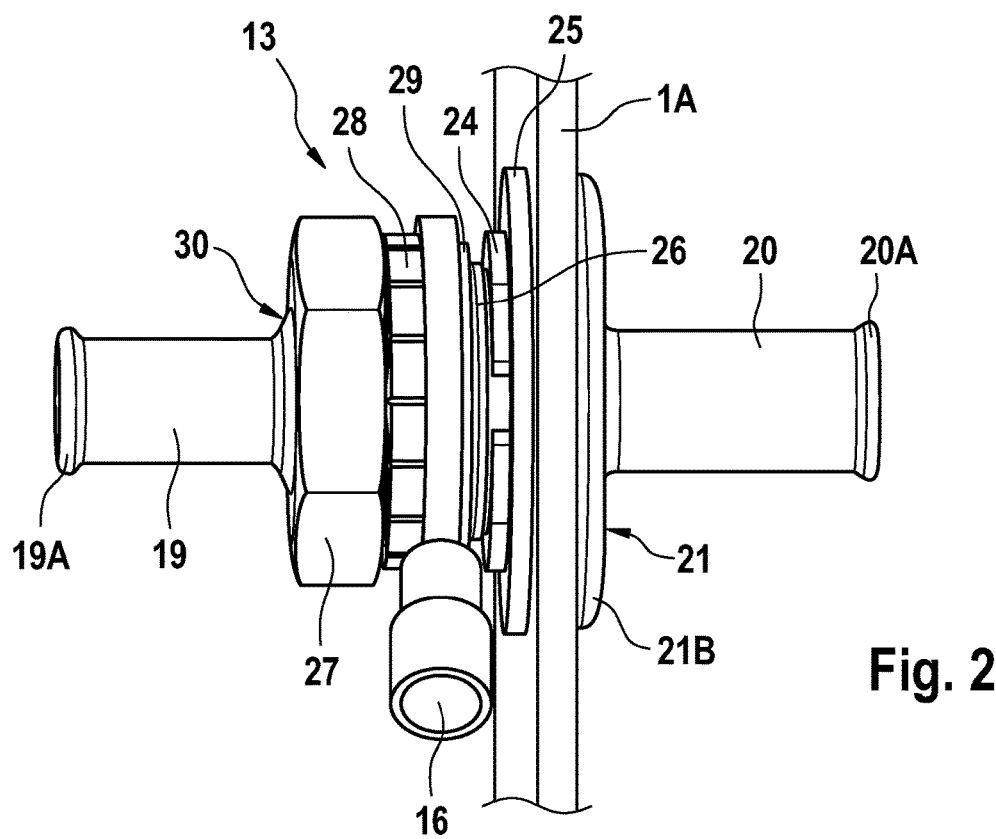
Figure 3:
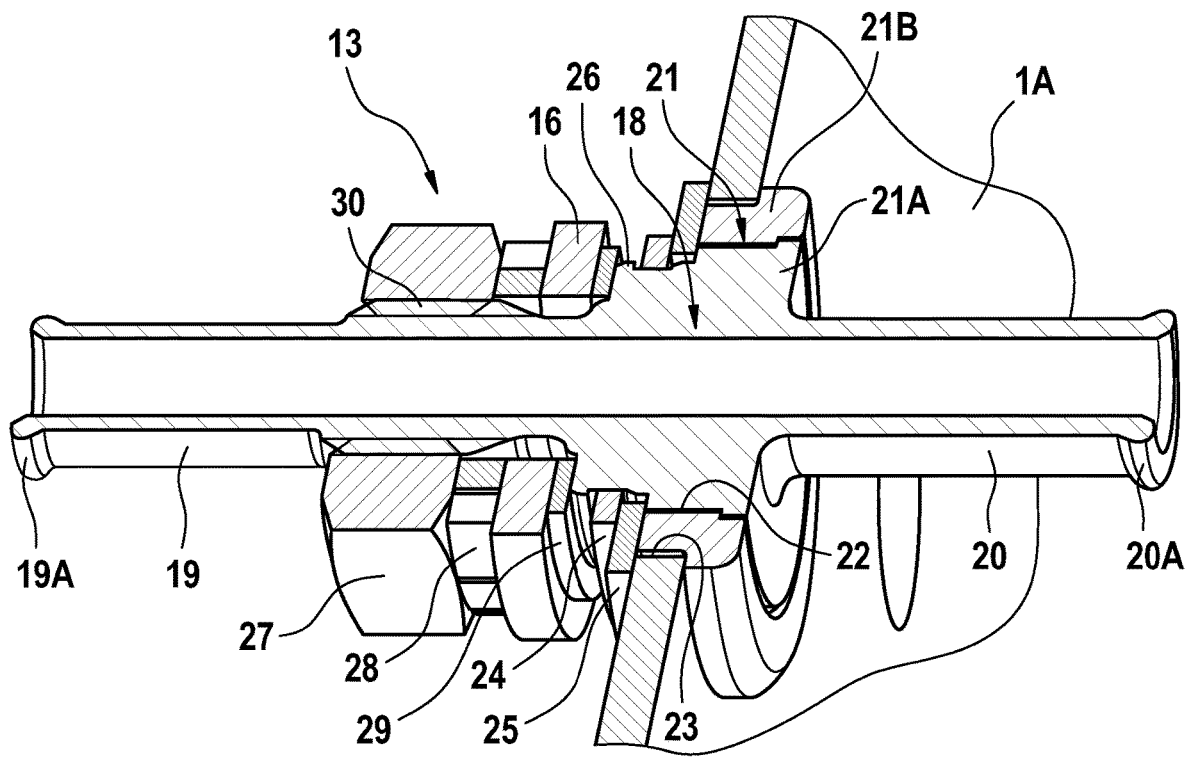
Figure 4:
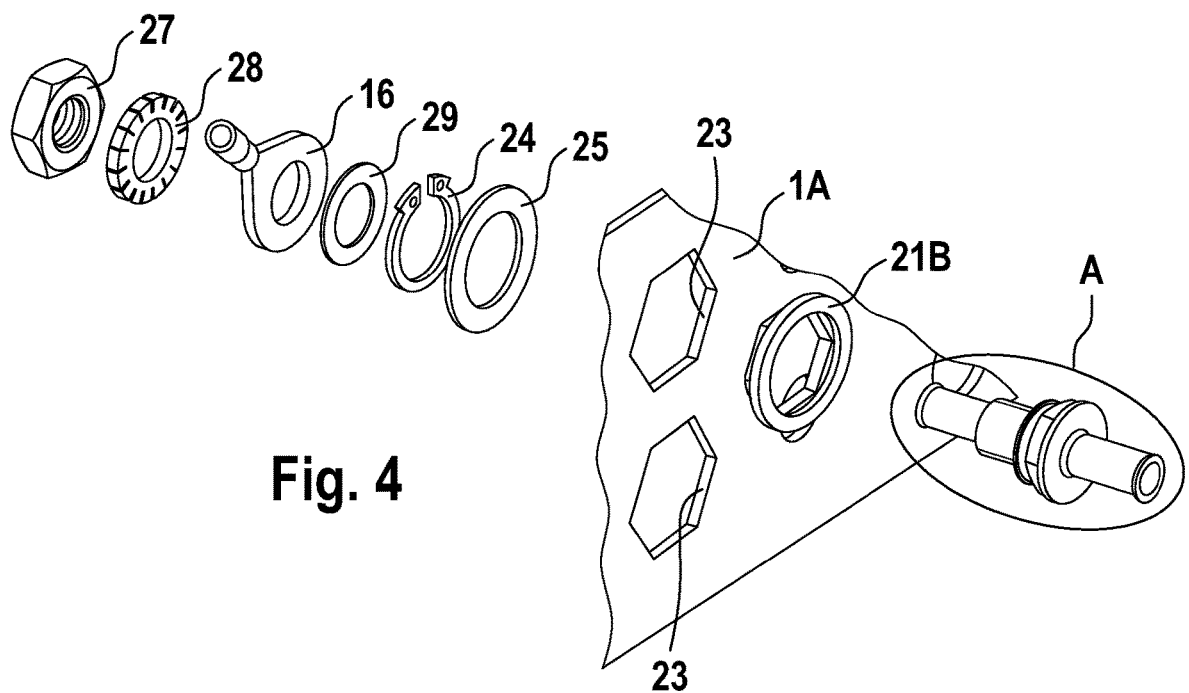
Figure 5:
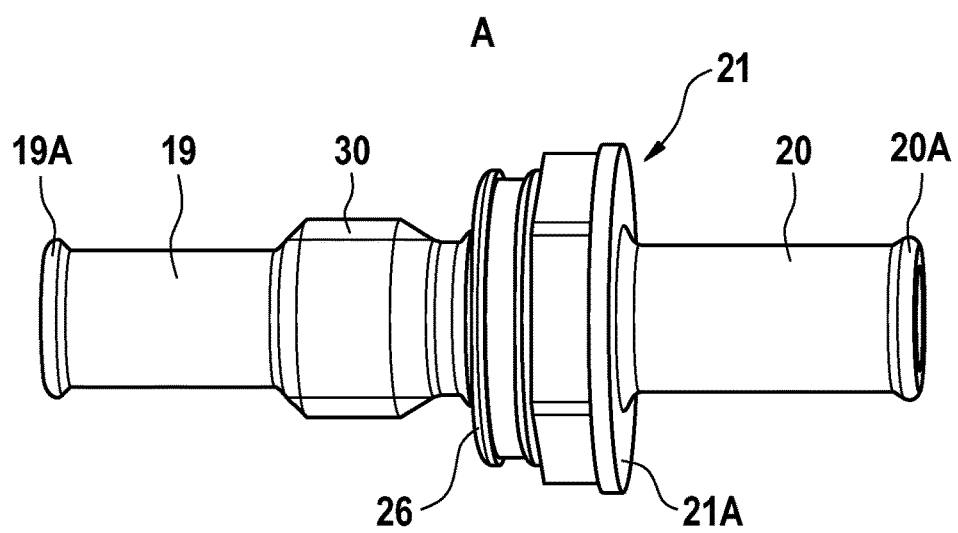

An embodiment of the invention is explained in more detail below with reference to the drawings, in which:

FIG. 1 is a highly simplified, schematic view of a part of the housing of a dialysis unit comprising the connecting pieces according to the invention, FIG. 2 is a side view of the connecting piece according to the invention, FIG. 3 is a sectional view of the connecting piece, FIG. 4 is an exploded view of the connecting piece and FIG. 5 is an enlarged view of the part A of the connecting piece from FIG. 4.

FIG. 1 is a highly simplified, schematic view of the components of a dialysis unit that are essential to the invention as an example of a medical device. The dialysis unit comprises a housing 1, which consists of an electrically conductive material (metal housing). The housing 1 may consist of a plurality of housing parts.

The dialysis unit comprises a dialyser 2, which is only shown schematically in FIG. 1 and is divided into a blood chamber 4 and a dialysate chamber 5 by a semi-permeable membrane 3. The dialyser 2 may be attached to a mount 6, which is provided on the outside of the housing 1. A blood feed line 7 leads to the blood chamber 4 of the dialyser 2 and a blood removal line 8 leads away from the blood chamber 4. The blood chamber 4 and the blood feed line 7 and blood removal line 8 form the extracorporeal blood circuit.

The dialysis unit has a dialysate part 9 that comprises an apparatus 10 for producing dialysate from fresh water and concentrates. A dialysate feed line 11 leads to an inlet of the dialysate chamber 5 from the apparatus 10 for producing dialysate and a dialysate removal line 12 leads to this apparatus 10 or a drain from an outlet of the dialysate chamber 5. The dialysate lines 10, 11 each comprise two line portions 11A, 11B, 12A, 12B that are attached to the connecting pieces 13 according to the invention, which are only shown schematically in FIG. 1.

Furthermore, the dialysis unit comprises a power unit 14 that has a central protective-conductor connection 15 or protective-conductor contact in the housing 1. The connecting pieces 13 comprise a terminal part 16 that is only shown schematically in FIG. 1 and is connected to the central protective-conductor connection 15 by an electrical connection cable 17. When the power unit 14 is attached to the mains, an electrical connection is established between the central protective-conductor connection 15 and the protective-conductor system of the fixed electrical installation.

In the following, an embodiment of the connecting piece 13 according to the invention is described in detail with reference to FIGS. 2 to 5. Here, reference is made to the housing part 1A, on which the connecting pieces 13 according to the invention are provided. FIG. 2 is a side view and FIG. 3 shows a section through the connecting piece.

The connecting piece 13 comprises a tubular body 18 made of metal material, for example stainless steel. The two end pieces 19, 20 of the tubular body are designed as terminal pieces for the line portions 11A, 11B, 12A, 12B of the dialysate lines 11, 12. Said end pieces comprise a circumferential bead 19A, 20A at the ends, such that the hose lines can be slid on and secured against being pulled off. Tube clamps or the like can be provided for secure attachment.

The tubular body 18 has a two-piece flange 21 that comprises an inner flange part 21A that is formed in one piece with the tubular body, and an outer flange part 21B. The outer flange part 21B comprises a cut-out 22 into which the inner flange part 21A can be fitted. The cut-out 22 in the outer flange part 21B and the peripheral surface of the inner flange part 21A are polygonal, and therefore the inner flange part is seated in the outer flange part such that it cannot twist. The outer flange part 21B can in turn be inserted into a corresponding polygonal cut-out 23 in the housing part 1A, and therefore the outer flange part is seated in the housing such that it cannot twist. The inner flange part 21A consists of an electrically non-conductive material; for example, the inner flange part is a plastics insulating washer.

FIG. 4 is an exploded view in which the polygonal cut-out 23 can be seen in the housing part 1A. FIG. 5 is an enlarged view of the tubular body 18 together with the inner flange part 21A.

If the outer flange part 21B is inserted into the cut-out 23 in the housing part 1A and the inner flange part 21A is inserted into the outer flange part 21B, the connecting piece 13 is supported on the housing part 1A. The connecting piece 13 is secured in the housing part 1A by a preferably metal securing ring 24, which is seated in a groove in the tubular body 18. There is a washer 25 made of an electrically non-conductive material, for example a plastics washer, between the flange 21 and the securing ring 24. As a result, the tubular body 18 is electrically insulated from the housing part 1A.

In the embodiment, the terminal part of the connecting piece 13 for attaching the protective conductor is a ring cable lug 16, which can be screwed to the tubular body 18. For this purpose, the tubular body 18 comprises a circumferential shoulder 26, which is arranged beside the securing ring 24 in the axial direction. An external thread 30, onto which a nut 27 can be screwed, is attached to the circumferential shoulder 26 in the axial direction. The ring cable lug 16 is fastened in a force-locked manner when the nut 27 is tightened. There is a serrated lock washer 28 between the nut 27 and the ring cable lug 16, and there is a metal washer 29 between the ring cable lug 16 and the circumferential shoulder 26. The connection cable 17 leading to the central protective-conductor connection 15 is attached to the ring cable lug 16. The cable can be attached to the ring cable lug using known connection techniques.

The invention claimed is:

1. A medical device comprising a housing that comprises a housing part having a cut-out, into which a connecting piece is inserted, and wherein said connecting piece is for establishing a fluid connection between fluid-conducting lines for installation in a cut-out in the housing part, said connecting piece comprising a tubular body that is made of an electrically conductive material and insertable into the cut-out in the housing part, and end pieces of the tubular body are designed for the attachment of the fluid-conducting lines, and the connecting piece further comprises a terminal part for attaching an electrical protective conductor or equipotential bonding system, the terminal part being electrically conductively connectable or connected to the tubular body.

2. The medical device according to claim 1, wherein the housing part consists of an electrically conductive material.

3. The medical device according to claim 1, wherein the medical device has a power unit comprising a central protective-conductor connection, and in that the terminal part of the connecting piece is electrically connected to the central protective-conductor connection by an electrical connection cable.

4. The medical device according to claim 1, wherein the medical device comprises a fluid part having fluid-conducting lines, the fluid-conducting lines being attached to the end pieces of the connecting piece.

5. The medical device according to claim 1, wherein the medical device is a dialysis unit that comprises a dialysate part having a dialysate feed line that leads to a dialyser and a dialysate removal line that leads away from the dialyser, one portion of the dialysate feed line or dialysate removal line being attached to one end piece and another portion of the dialysate feed line or dialysate removal line being attached to the other end piece of the connecting piece.

6. The medical device of claim 1, wherein the medical device is a dialysis unit.

7. The medical device of claim 1, wherein the terminal part is a ring cable lug that is screwable to the tubular body.

8. The medical device of claim 1, wherein the tubular body comprises a circumferential shoulder to which an external thread is attached.

9. The medical device of claim 1, wherein the terminal part is a terminal lug that is electrically conductively connected to the tubular body.

10. A medical device comprising a housing, the housing comprising a housing part having a cut-out into which a connecting piece is inserted, the connecting piece establishes a fluid connection between fluid-conducting lines, the connecting piece comprising a tubular body comprising an electrically conductive material and insertable into the cut-out in the housing part, and wherein end pieces of the tubular body are designed for the attachment of the fluid-conducting lines, and the connecting piece further comprises a terminal part for attaching an electrical protective conductor or equipotential bonding system, the terminal part being electrically conductively connectable or connected to the tubular body, wherein the tubular body comprises, between the end pieces, a flange by means of which the tubular body is supportable on the housing part, and comprises a securing part that is attachable to the tubular body such that the tubular body is secured in the cut-out in the housing part in an axial direction.

11. The medical device of claim 10, wherein the flange of the tubular body comprises an inner flange part that is formed in one piece with the tubular body and an outer flange part that comprises a cut-out into which the inner flange part is insertable, and wherein the tubular body is capable of being supported on the housing part by the outer flange part, and the outer flange part consisting of an electrically non-conductive material.

12. The medical device of claim 11, wherein the inner flange part is secured against twisting in the outer flange part.

13. The medical device of claim 11, wherein the outer flange part comprises a polygonal cut-out, and the inner flange part comprises a polygonal peripheral surface.

14. The medical device of claim 10, wherein the securing part is a securing ring that is attachable to the tubular body.

15. The medical device of claim 14, wherein the connecting piece comprises a washer that is made of an electrically non-conductive material and is insertable between the securing ring and the flange of the tubular body.

* * * * *